US00PP34076P2

(12) United States Plant Patent
Magee

(10) Patent No.: US PP34,076 P2
(45) Date of Patent: Mar. 29, 2022

(54) CRAPEMYRTLE PLANT NAMED 'JM8'

(50) Latin Name: ***Lagerstroemia indica* JM8**
Varietal Denomination: JM8

(71) Applicant: Jack Mitchell Magee, Poplarville, MS (US)

(72) Inventor: Jack Mitchell Magee, Poplarville, MS (US)

(73) Assignees: GREENLEAF NURSERY Co., Park Hill, OK (US); EVERGREEN NURSERY, Poplarville, MS (US)

( * ) Notice: Subject to any disclaimer, the term of this patent is extended or adjusted under 35 U.S.C. 154(b) by 0 days.

(21) Appl. No.: 17/162,166

(22) Filed: Jan. 29, 2021

(51) Int. Cl.

| | |
|---|---|
| ***A01H 5/00*** | (2018.01) |
| ***A01H 6/00*** | (2018.01) |
| ***A01H 5/02*** | (2018.01) |

(52) U.S. Cl.
USPC ..... Plt./252
CPC ..... *A01H 6/00* (2018.05); *A01H 5/02* (2013.01)

(58) Field of Classification Search
USPC ..... Plt./252
See application file for complete search history.

*Primary Examiner* — Susan McCormick Ewoldt
(74) *Attorney, Agent, or Firm* — C. Anne Whealy

(57) ABSTRACT

A new and distinct cultivar of Crapemyrtle plant named 'JM8', characterized by its upright to somewhat outwardly spreading plant habit; freely branching habit; vigorous and sturdy growth habit and rapid growth rate; dark greyed purple-colored leaves; numerous inflorescences with lavender-colored flowers; and good garden performance and pathogen resistance.

2 Drawing Sheets

Figure 1:
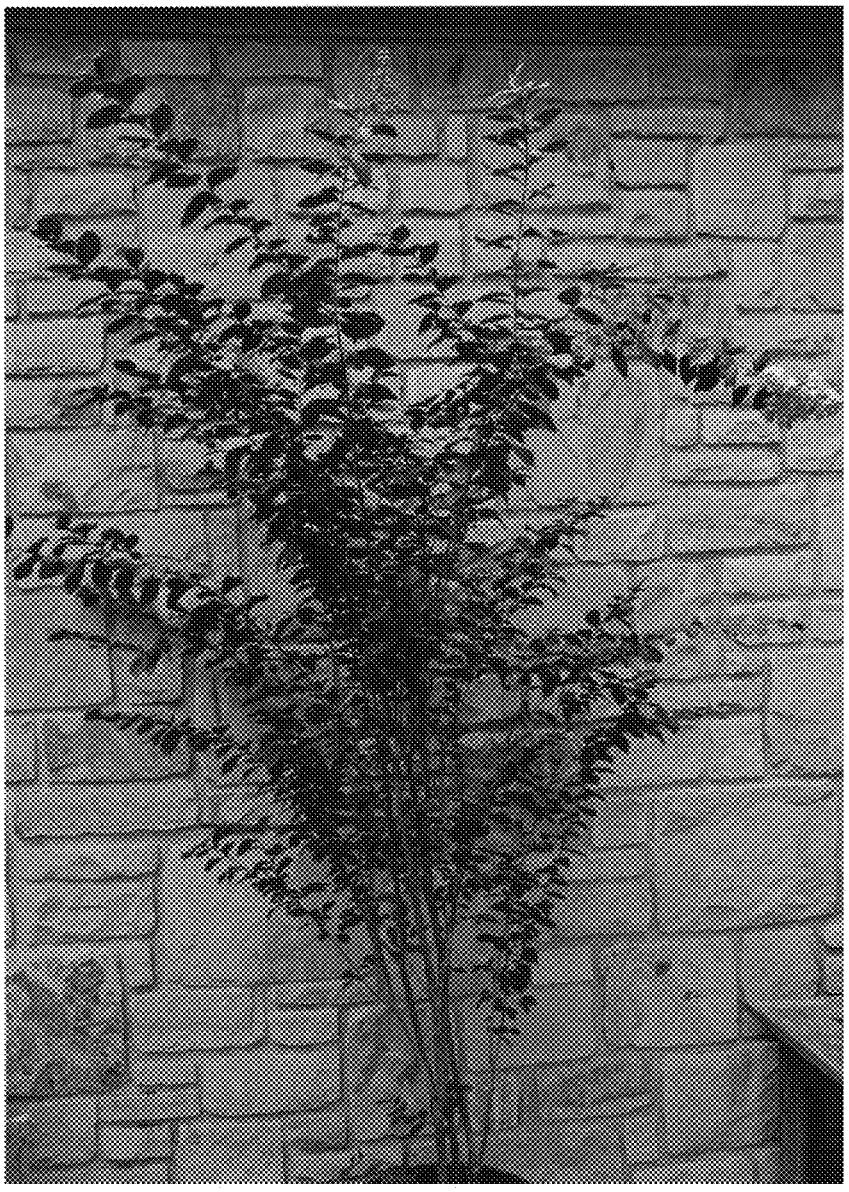

Botanical designation: *Lagerstroemia indica* 'JM8'.
Cultivar denomination: 'JM8'.

STATEMENT REGARDING PRIOR DISCLOSURES BY INVENTOR/APPLICANT

The Inventor/Applicant hereby assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of Crapemyrtle plant, botanically known as *Lagerstroemia indica* 'JM8' and hereinafter referred to by the name 'JM8'.

The new Crapemyrtle plant is a product of a planned breeding program conducted by the Inventor in Poplarville, Miss. The objective of the breeding program was to develop new vigorous and freely-branching Crapemyrtle plants with dark-colored leaves and attractive flower colors.

The new Crapemyrtle plant originated from a cross-pollination conducted by the Inventor during the summer of 2016 of *Lagerstroemia indica* 'Natchez White', not patented, as the female, or seed, parent with *Lagerstroemia indica* 'Ebony Flame', not patented, as the male, or pollen, parent. The new Crapemyrtle plant was discovered and selected by the Inventor in May, 2017 as a single flowering plant from within the progeny of the stated cross-pollination in a controlled nursery environment in Poplarville, Miss.

Asexual reproduction of the new Crapemyrtle plant by vegetative softwood cuttings in a controlled greenhouse environment in Poplarville, Miss. since August, 2017 has shown that the unique features of the new Crapemyrtle plant are stable and reproduced true to type in successive generations of asexual reproduction.

SUMMARY OF THE INVENTION

Plants of the new Crapemyrtle have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JM8'. These characteristics in combination distinguish 'JM8' as a new and distinct Crapemyrtle plant:

1. Upright to somewhat outwardly spreading plant habit.
2. Freely branching habit.
3. Vigorous and sturdy growth habit and rapid growth rate.
4. Dark greyed purple-colored leaves.
5. Numerous inflorescences with lavender-colored flowers.
6. Good garden performance and pathogen resistance.

Plants of the new Crapemyrtle can be compared to plants of the female parent, 'Natchez White'. Plants of the new Crapemyrtle differ primarily from plants of 'Natchez White' in the following characteristics:

1. Leaves of plants of the new Crapemyrtle are dark greyed purple in color whereas leaves of plants of 'Natchez White' are light green in color; in addition, in the autumn, leaves of plants of the new Crapemyrtle maintain their dark greyed purple color whereas in the autumn, leaves of plants of 'Natchez White' turn orange in color.

2. Flowers of plants of the new Crapemyrtle are lavender in color whereas flowers of plants of 'Natchez White' are white in color.

Plants of the new Crapemyrtle can be compared to plants of the male parent, 'Ebony Flame'. Plants of the new Crapemyrtle differ primarily from plants of 'Ebony Flame' in the following characteristics:

1. Plants of the new Crapemyrtle are more vigorous and faster growing than plants of 'Ebony Flame'.
2. Flowers of plants of the new Crapemyrtle are lavender in color whereas flowers of plants of 'Ebony Flame' are red in color.

Plants of the new Crapemyrtle can be compared to plants of *Lagerstroemia indica*, 'Catawba', not patented. Plants of the new Crapemyrtle differ primarily from plants of 'Catawba' in the following characteristics:

1. Leaves of plants of the new Crapemyrtle are dark greyed purple in color whereas leaves of plants of 'Catawba' are green in color; in addition, in the autumn, leaves of plants of the new Crapemyrtle maintain their dark greyed purple color whereas in the autumn, leaves of plants of 'Catawba' turn orange red in color.
2. Flowers of plants of the new Crapemyrtle are lavender in color whereas flowers of plants of 'Catawba' are dark purple in color.

Plants of the new Crapemyrtle can also be compared to plants of *Lagerstroemia indica*, 'Muskogee', not patented. Plants of the new Crapemyrtle differ primarily from plants of 'Muskogee' in the following characteristics:

1. Leaves of plants of the new Crapemyrtle are dark greyed purple in color whereas leaves of plants of 'Muskogee' are dark green in color.
2. Flowers of plants of the new Crapemyrtle are lavender in color whereas flowers of plants of 'Muskogee' are purple in color.
3. Inflorescences of plants of the new Crapemyrtle are smaller than inflorescences of plants of 'Muskogee'.
4. Plants of the new Crapemyrtle are resistant to leaf spot (*Cercospora lythracearum*) whereas plants of 'Muskogee' are not resistant to leaf spot.
5. Plants of the new Crapemyrtle are more resistant to powdery mildew (*Erysiphe lagerstroemia*) than plants of 'Muskogee'.

BRIEF DESCRIPTION OF THE PHOTOGRAPHS

The accompanying colored photographs illustrate the overall appearance of the new Crapemyrtle plant showing the colors as true as it is reasonably possible to obtain in colored reproductions of this type. Colors in the photographs may differ slightly from the color values cited in the detailed botanical description which accurately describe the colors of the new Crapemyrtle plant.

The photograph on the first sheet (FIG. 1) is a side perspective view of a typical plant of 'JM8' grown in a container in an outdoor nursery.

Figure 2:
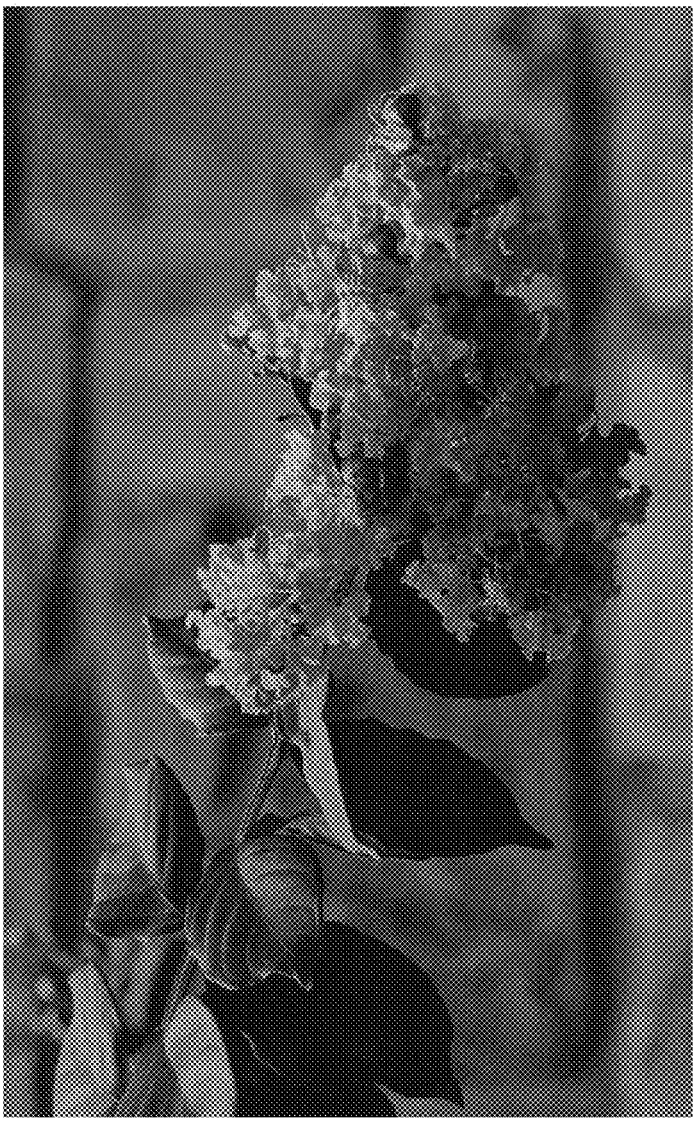

The photograph on the second sheet (FIG. 2) is a close-up view of a typical flowering stein of 'JM8' grown in a container in an outdoor nursery.

DETAILED BOTANICAL DESCRIPTION

The aforementioned photographs and following observations, measurements and values describe plants grown in 7-gallon containers in Park Hill, Okla. and Fort Worth, Tex. during the summer and early autumn in outdoor nurseries and under cultural conditions which closely approximate commercial Crapemyrtle production. During the production of the plants, day temperatures averaged 33° C. and night temperatures averaged 14° C. Plants were three years when the photographs and the description were taken. In the following description, color references are made to The Royal Horticultural Society Colour Chart, 2015 Edition, except where general terms of ordinary dictionary significance are used.

Botanical classification: *Lagerstroemia indica* 'JM8'.

Parentage:

*Female, or seed, parent.*—*Lagerstroemia indica* 'Natchez White', not patented.

*Male, or pollen, parent.*—*Lagerstroemia indica* 'Ebony Flame', not patented.

Propagation:

*Type*.—By vegetative softwood and hardwood cuttings.

*Time to initiate roots, summer*.—About ten days at temperatures about 21° C. to 33° C.

*Time to initiate roots, winter*.—About 25 days at temperatures about 21° C. to 33° C.

*Time to produce a rooted young plant, summer*.—About one month at temperatures about 21° C. to 33° C.

*Time to produce a rooted young plant, winter*.—About one month for softwood cuttings and about two months for hardwood cuttings at temperatures about 21° C. to 33° C.

*Root description*.—Medium in thickness, fibrous; typically brownish white in color, actual color is dependent on substrate composition, water quality, fertilizer type and formulation, substrate temperature and physiological age of roots.

*Rooting habit*.—Freely branching; dense.

Plant description:

*Plant form and growth habit*.—Perennial shrub; upright to somewhat outwardly spreading plant habit; vigorous and sturdy growth habit; rapid growth rate.

*Branching habit*.—Freely branching habit with about four to six primary branches each with numerous secondary and tertiary lateral branches developing per plant.

*Plant height*.—About 2 meters.

*Plant diameter* (*area of spread*).—About 110 cm to 120 cm.

Lateral branch description:

*Length*.—About 110 cm.

*Diameter, proximally*.—About 1.5 cm.

*Internode length*.—About 1.2 cm to 2 cm.

*Strength*.—Strong.

*Aspect*.—About 45° from vertical.

*Texture and luster*.—Pubescent; woody and glabrous with age; matte.

*Color, immature*.—Close to 185A and 183A to 183B.

*Color, mature*.—Close to 177A becoming closer to 199B to 199C.

Leaf description:

*Arrangement*.—Alternate; simple.

*Length*.—About 3.5 cm to 4.5 cm.

*Width*.—About 2 cm to 2.5 cm.

*Shape*.—Ovate.

*Apex*.—Acute to acuminate.

*Base*.—Obtuse with cuneate tendencies.

*Margin*.—Entire; developing leaves, slightly to moderately undulate; developed leaves, not undulate.

*Texture and luster, upper surface*.—Smooth, glabrous; dull.

*Texture and luster, lower surface*.—Smooth, glabrous; semi-glossy.

*Venation pattern*.—Pinnate.

*Color*.—Developing leaves, upper surface: Close to 147A to 147B becoming closer to N186A. Developing leaves, lower surface: Close to 146A becoming closer to N186C. Fully expanded leaves, upper surface: Close to N186A; venation, close to 183A and N186A. Fully expanded leaves, lower surface: Close to more green than 183A; venation, close to 186A and 183A.

*Petioles*.—Length: About 1 mm to 1.5 mm. Diameter: About 1 mm. Texture and luster, upper and lower surfaces: Smooth, glabrous; somewhat glossy. Strength: Strong. Color, upper surface: Close to 147A overlain with close to 186A. Color, lower surface: Close to 183A.

Flower description:

*Flower type, arrangement and habit*.—Showy single ruffled flowers arranged in terminal panicles; freely flowering habit with usually about 50 flower buds and flowers developing per inflorescence and numerous inflorescences developing during the flowering season; flowers face upright and outwardly; flowers not persistent.

*Natural flowering season*.—Plants of the new Crapemyrtle flower during the late summer and autumn in Central Texas.

*Fragrance*.—None detected.

*Inflorescence height*.—About 7 cm to 12 cm.

*Inflorescence diameter*.—About 5 cm to 7 cm.

*Flower length*.—About 1.9 cm to 3 cm.

*Flower diameter*.—About 2.7 cm to 3.25 cm.

*Flower depth*.—About 1.5 cm to 2 cm.

*Flower buds*.—Length: About 6 mm to 7 mm. Diameter: About 5 mm to 6 mm. Shape: Obovate to spherical. Texture and luster: Smooth, glabrous; slightly glossy. Color: Close to 184A.

*Petals*.—Quantity per flower and arrangement: Six arranged in a single whorl. Length: About 1 cm. Width: About 1.1 cm. Shape: Roughly orbicular. Apex: Rounded, undulate, ruffled appearance. Base: Rounded. Margin: Mostly entire with shallow sinuation, undulate, ruffled appearance. Texture and luster, upper and lower surfaces: Smooth, glabrous; soft/velvety; delicate; matte. Color: When opening, upper and lower surfaces: Close to NN74C. Fully opened, upper and lower surfaces: Close to NN74C; colors do not change with development.

*Sepals*.—Quantity per flower and arrangement: Five or six arranged in a single whorl. Length: About 3 mm. Width: About 2.5 mm. Shape: Deltoid. Apex: Acute. Base: Fused. Margin: Entire. Texture and luster, upper surface: Smooth, glabrous; semi-glossy. Texture and luster, lower surface: Smooth, glabrous; slightly glossy. Color: When opening and fully opened, upper surface: Close to 186B. When opening and fully opened, lower surface: Close to 184A.

*Pedicels*.—Length: About 8 mm. Diameter: About 1 mm to 1.5 mm. Strength: Strong, flexible. Aspect: About 45° to 50° from stein axis. Texture and luster: Smooth, glabrous; slightly glossy. Color: Proximally, close to 59A to 59B; distally, close to 144A.

*Reproductive organs*.—Androecium: Quantity per flower: About 12 to 24. Filament length: About 7 mm to 9 mm. Filament color: Close to 184A. Anther length: About 1 mm. Anther shape: Oblong. Anther color: Close to 7A. Amount of pollen: None observed. Gynoecium: Quantity per flower: One. Pistil length: About 1 cm. Style length: About 9 mm. Style color: Close to 58A to 58B to 55A. Stigma appearance: Spherical to oblong. Stigma color: Close to NN137A becoming closer to 55A with development. Ovary: Close to 7A becoming closer to 10B to 10C with development.

*Fruits and seeds*.—To date, fruit and seed development has not been observed on plants of the new Crapemyrtle.

Garden performance: Plants of the new Crapemyrtle have been observed to have good garden performance and to tolerate rain, wind and temperatures ranging from about −10° C. to about 38° C. and to be cold hardy to USDA Hardiness Zone 6.

Pathogen & pest resistance: Plants of the new Crapemyrtle have been observed to be resistant to leaf spot (*Cercospora lythracearum*) and powdery mildew (*Erysiphe lagerstroemia*). Plants of the new Crapemyrtle have not been observed to be resistant to pests and other pathogens common to Crapemyrtle plants.

It is claimed:

1. A new and distinct Crapemyrtle plant named 'JM8' as illustrated and described.

* * * * *